United States Patent [19]

Frank et al.

[11] Patent Number: 4,900,122
[45] Date of Patent: Feb. 13, 1990

[54] DEVICE FOR A FIBER-OPTIC GUIDE

[75] Inventors: Frank Frank, Ebersberg; Thomas Hengst, Haar; Andreas Hahn, Sauerlach, all of Fed. Rep. of Germany

[73] Assignee: Messerschmitt-Bölkow-Blohm GmbH, Munich, Fed. Rep. of Germany

[21] Appl. No.: 289,929

[22] Filed: Dec. 23, 1988

[30] Foreign Application Priority Data

Mar. 7, 1988 [DE] Fed. Rep. of Germany ....... 3807437

[51] Int. Cl.⁴ .............................................. G02B 6/36
[52] U.S. Cl. .............................. 350/96.20; 350/96.26
[58] Field of Search ............... 350/96.20, 96.24, 96.26, 350/96.10

[56] References Cited

U.S. PATENT DOCUMENTS

| 4,597,030 | 6/1986 | Brody et al. | 350/96.26 X |
| 4,611,888 | 9/1986 | Prehovitz et al. | 350/96.26 X |
| 4,669,819 | 6/1987 | Hengst et al. | 350/96.26 X |
| 4,696,537 | 9/1987 | Bauer et al. | 350/96.20 |
| 4,756,597 | 7/1988 | Hahn et al. | 350/96.10 X |
| 4,770,443 | 9/1988 | Yamamoto | 350/96.26 X |

Primary Examiner—John D. Lee
Assistant Examiner—Phan T. Heartney
Attorney, Agent, or Firm—Kenyon & Kenyon

[57] ABSTRACT

A device for allowing the adjustment of the length of a fiber optic waveguide is disclosed. The device couples casings of different inner and outer diameters together, while allowing for the movement of the fiber optic waveguide within the casings. The device is useful for adapting the fiber optic guide to different instruments, such as endoscopes.

3 Claims, 1 Drawing Sheet

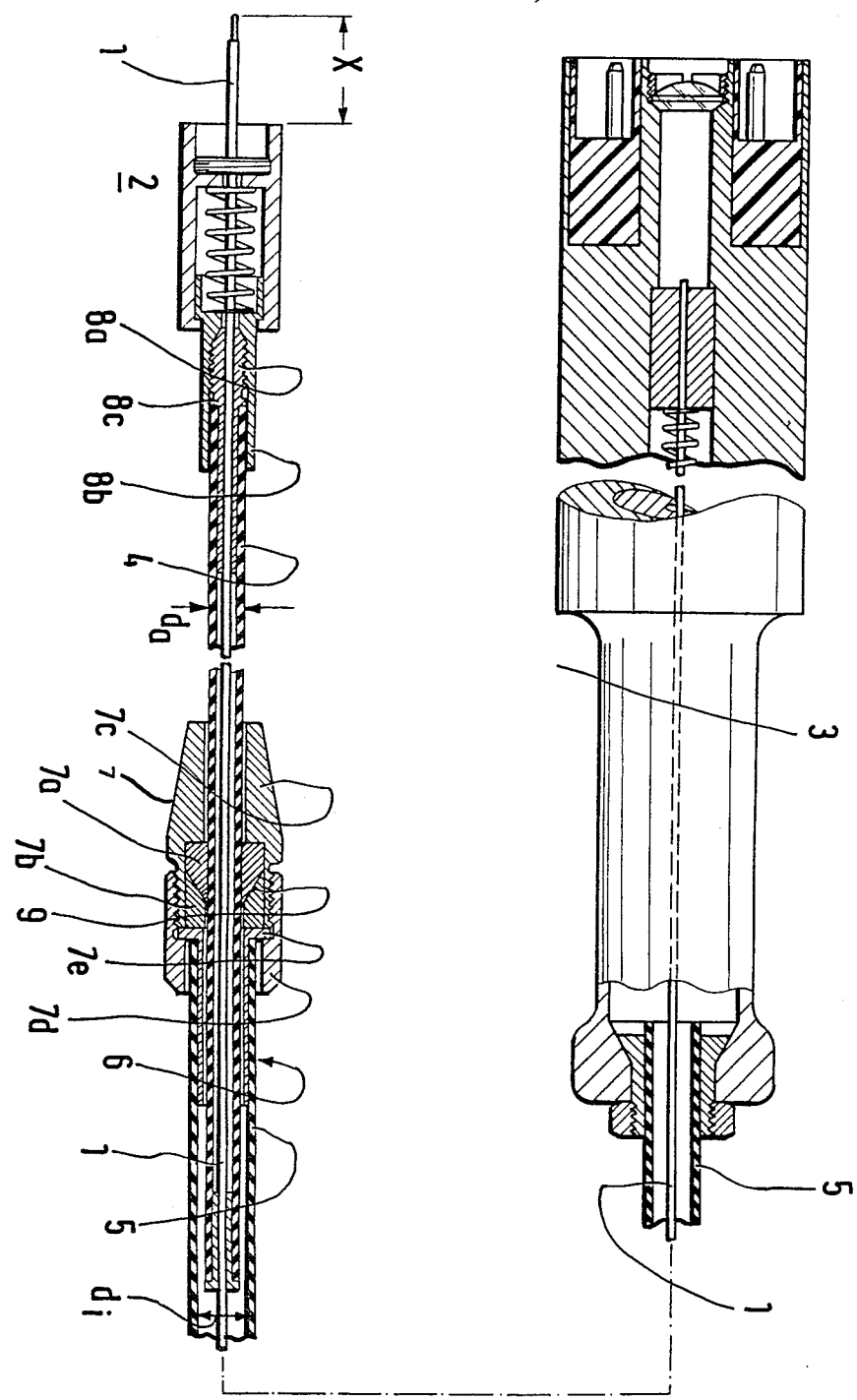

DEVICE FOR A FIBER-OPTIC GUIDE

FIELD OF THE INVENTION

This invention relates to the field of fiber optic waveguides. More specifically it relates to a device for coupling fiber optic waveguide casings of different diameters together.

BACKGROUND OF THE INVENTION

Devices for coupling a fiber optic waveguide to both a medical laser and an endoscope, where the operating end of the endoscope has a longitudinal feed device for the fiber optic waveguide, are known.

One such fiber optic waveguide is described in German Patent No. 2,945,080. The connecting piece of the endoscope has a longitudinal feed device for the fiber optic waveguide. This enables the distal end of the fiber optic waveguide to emerge from the endoscope by a few millimeters, in reverse if necessary, so that the tip of the fiber optic waveguide can be cleaned during a treatment. This device only allows the length of the emerging fiber optic waveguide to be modified by a small distance, however.

It is an object of this invention to design a fiber optic waveguide connection between a medical laser and an endoscope which will allow the fiber optic waveguide emerging from the connecting piece of the endoscope to be adjusted to any length, up to one meter. This permits the fiber optic waveguide to be adapted for use with different endoscopes while allowing the longitudinal feed device for the fiber optic waveguide to fulfill its purpose.

SUMMARY OF THE INVENTION

These objectives and others are fulfilled by the present invention in which the fiber optic waveguide is disposed within a first casing having an inner diameter of $d_i$ and a second casing having an outer diameter $d_a$, diameter $d_a$ being less than diameter $d_i$. The second casing is inserted into the first casing and, at the point where the second casing enters the first, a detachable clamp is attached, which couples the first and second casings together. At the longitudinal feed device on the endoscope, the second casing is coupled to the fiber optic waveguide by a second detachable clamp.

The special advantage of the adapter is that for each endoscope using a matched connection, the fiber optic waveguide which emerges from the connecting piece can be adjusted to any length, allowing a large reduction in the inventory of fiber optic waveguides. Additionally, over a period of time a fiber optic waveguide can be used repeatedly by trimming its distal tip, whereas previously, if any damage occurred, the entire fiber optic waveguide had to be replaced. Finally, the rigid optic guide casings act as both protective sleeves and strain relief devices for the fiber optic waveguide.

These and other objects and advantages of the invention will appear more clearly from the following specification in connection with the accompanying drawing, in which:

BRIEF DESCRIPTION OF THE DRAWING

The FIGURE shows a schematically simplified cross-section of the present invention.

DETAILED DESCRIPTION

Referring to the FIGURE, fiber optic waveguide 1 and fiber optic waveguide casing 5 are fixed to connecting piece 3 which is in turn is coupled to a medical laser (not shown). Fiber optic waveguide casing 5 has an inner diameter of $d_i$. At junction point 6, smaller fiber optic waveguide casing 4, which has an outer diameter of $d_a$ which is smaller than inner diameter $d_i$ of fiber optic waveguide casing 5, is inserted into fiber optic waveguide casing 5. Both casings 4 and 5 are comprised of a flexurally stiff material. The material can be a metal spiral coated with plastic. Fiber optic waveguide 1 is loosely supported inside fiber optic waveguide casings 4 and 5.

Fiber optic casings 4 and 5 are locked together by a first detachable clamping connection 7. First detachable clamping connection 7 is comprised of collets 7a and 7b, metal sleeves 7c and 7d and plastic sleeve 7e. Fiber optic waveguide casing 5 is slid onto plastic sleeve 7e and bonded to it. Clamping is accomplished by means of two collets 7a and 7b, here made from plastic, which abut one another in the form of a conical parting plane 9. Collet 7a lying within the conical area can be of a slotted construction.

Metal sleeve 7c, which contains collet 7a, has a male screw coupling. Metal sleeve 7d, which contains collet 7b and sleeve 7e, has a female screw coupling. Clamping occurs when metal sleeves 7c and 7d are screwed together, which in turn clamps collets 7a and 7b together tightly along a common axial direction.

Fiber optic casing 4 is coupled to fiber optic waveguide/feed device 2 in a similar manner. Fiber optic casing 4 is slid onto plastic sleeve 8c and bonded to it. Metal sleeve 8a has a male screw coupling and metal sleeve 8b has a female screw coupling. By screwing sleeves 8b and 8a together, plastic sleeve 8c and fiber optic casing 4 are tightly clamped to fiber optic waveguide/feed device 2. This coupling also serves to couple fiber optic waveguide 1 to fiber optic waveguide casing 4.

Using this adapter, the length X of fiber optic waveguide 1 emerging from fiber optic waveguide/feed device 2 can now be easily adjusted within the range specified by the length of fiber optic waveguide casings 4 and 5. To adjust the length, the clamping on fiber optic waveguide/feed device 2 is released. Then the clamping at junction point 6 is released. After the length is adjusted, the clampings are tightened in reverse order.

In the foregoing specification, the invention has been described with reference to specific exemplary embodiments thereof. It will, however, be evident that various modifications and changes may be made thereunto without departing from the broader spirit and scope of the invention as set forth in the appended claims. The specification and drawings are, accordingly, to be regarded in an illustrative rather than in a restrictive sense.

What is claimed is:

1. A device for a fiber optic waveguide to attach the fiber optic waveguide to a medical laser and to an endoscope, the operating end of the endoscope having a longitudinal feed device for the fiber optic waveguide, the device comprising:

first rigid fiber optic waveguide casing means having a preset inner diameter;

second rigid fiber optic waveguide casing means having a preset outer diameter smaller than the preset inner diameter of the first casing means so that the second casing means can slide concentrically in the first casing means at a predetermined point;

fiber optic waveguide means disposed within the first and second waveguide casing means;

first detachable and adjustable clamping means for clamping the first and second casing means together at the predetermined point, said first detachable clamping means comprising collar means disposed around said second waveguide casing means and sleeve means surrounding said collar means and said first and second waveguide casing means for applying a force to said collar means thereby clamping said first and second waveguide casing means together at said predetermined point; and second detachable and adjustable clamping means for clamping the fiber optic waveguide means to the second casing means at the longitudinal feed device, whereby to adjust the amount of said fiber optic waveguide extending from said longitudinal feed device, said first and second detachable clamping means are loosened, the amount of said fiber optic waveguide extending from said longitudinal feed device desired is selected and said first and second detachable clamping means are then retightened to secure the adjustment.

2. The device recited in claim 1, wherein said collar means comprises first and second collar means disposed in abutting relationship about said first waveguide casing means.

3. The device recited in claim 2, wherein one of said collar means forms a frusto-conical surface in abutting relation with a mating surface of the other collar means.

* * * * *